(12) United States Patent
Chelli et al.

(10) Patent No.: US 12,294,180 B2
(45) Date of Patent: May 6, 2025

(54) FLUID SYSTEM CONNECTOR

(71) Applicant: Bellco S.R.L., Mirandola (IT)

(72) Inventors: Niccolo Chelli, Rufina (IT); Giuliano Giganti, Oppido Lucano (IT)

(73) Assignee: Bellco S.R.L., Mirandola (IT)

( * ) Notice: Subject to any disclaimer, the term of this patent is extended or adjusted under 35 U.S.C. 154(b) by 44 days.

(21) Appl. No.: 18/341,722

(22) Filed: Jun. 26, 2023

(65) Prior Publication Data

US 2023/0352875 A1    Nov. 2, 2023

Related U.S. Application Data

(63) Continuation of application No. 17/195,256, filed on Mar. 8, 2021, now Pat. No. 11,688,971.

(51) Int. Cl.
*H01R 13/62* (2006.01)
*H01R 13/24* (2006.01)

(52) U.S. Cl.
CPC ......... *H01R 13/6205* (2013.01); *H01R 13/24* (2013.01)

(58) Field of Classification Search
CPC ............................ H01R 13/6502; H01R 13/24
See application file for complete search history.

(56) References Cited

U.S. PATENT DOCUMENTS

| | | | |
|---|---|---|---|
| 4,317,969 A | 3/1982 | Riegler et al. | |
| 5,465,911 A * | 11/1995 | Hall | F02M 61/168 336/107 |
| 8,478,912 B2 | 7/2013 | Liu et al. | |
| 9,077,105 B2 | 7/2015 | Kim | |
| 9,685,742 B2 * | 6/2017 | Liu | H01H 37/002 |
| 9,985,384 B1 * | 5/2018 | Johnson | H01R 13/64 |
| 10,008,817 B2 | 6/2018 | Fullerton et al. | |
| 10,096,938 B2 | 10/2018 | McClelland | |
| 10,103,480 B2 * | 10/2018 | Zhang | H04M 1/02 |
| 10,298,037 B2 | 5/2019 | Wang et al. | |
| 10,454,208 B2 * | 10/2019 | Johnson | H01R 13/6456 |
| 10,468,842 B2 * | 11/2019 | Sun | H01R 31/065 |
| 10,627,083 B2 * | 4/2020 | Tuchler | H01R 13/6205 |
| 10,658,793 B2 | 5/2020 | Blake et al. | |
| 10,790,628 B2 * | 9/2020 | Landwehr | H01R 27/00 |
| 11,228,148 B2 | 1/2022 | Aridah et al. | |

(Continued)

OTHER PUBLICATIONS

Prosecution History from U.S. Appl. No. 17/195,256, dated Nov. 17, 2022 through May 30, 2023, 24 pp.

*Primary Examiner* — Thanh Tam T Le

(57) ABSTRACT

A connector including a plug configured to mechanically mate with a socket to establish a connection from a first conduit to a second conduit. The plug is configured to mechanically engage the first conduit and the socket is configured to mechanically engage the second conduit. In examples, the plug is configured to insert into a socket well of the socket. The connector includes an electromagnet configured to energize and produce a magnetic field when the plug mechanically mates with the socket. The electromagnet is configured such that the magnetic field generates an electromagnetic force on a plug armature of the plug to help sustain the mechanically mating of the plug and the socket. The connector may include a user device configured to provide an output indicating when the plug is mechanically mated or unmated with the socket.

20 Claims, 6 Drawing Sheets

(56) References Cited

U.S. PATENT DOCUMENTS

| | | | |
|---|---|---|---|
| 11,374,367 B2* | 6/2022 | Johnson | H01R 13/641 |
| 11,485,242 B2* | 11/2022 | Weber | H02J 7/0042 |
| 11,626,699 B2 | 4/2023 | Chelli et al. | |
| 11,757,229 B2* | 9/2023 | Johnson | H01R 13/629 |
| | | | 439/39 |
| 2017/0281847 A1 | 10/2017 | Manda et al. | |
| 2021/0022792 A1* | 1/2021 | Beaupre | A61B 18/1445 |
| 2022/0285880 A1 | 9/2022 | Chelli et al. | |
| 2022/0285893 A1 | 9/2022 | Chelli et al. | |

* cited by examiner

FLUID SYSTEM CONNECTOR

This application is a continuation of U.S. patent application Ser. No. 17/195,256, entitled, "FLUID SYSTEM CONNECTOR," and filed on Mar. 8, 2021, the entire content of which is incorporated herein by reference.

TECHNICAL FIELD

This disclosure is related to a fluid system connector.

BACKGROUND

Dialysis machines may be used to remove waste products from blood of a patient when the kidneys of the patient are no longer able to adequately do so. During dialysis, the dialysis machine may generate or regenerate dialysate using specified concentrations of solute buffers, osmotic agents, cations, and/or other concentrates for biocompatibility with the patient. The dialysis machine may provide the dialysate to a cycler for delivery to the patient. The generation or regeneration of dialysate may require a patient or another user to perform physical connections between disposable elements and the dialysis machine.

SUMMARY

This disclosure describes a connector configured to establish a connection between a container configured to store a material, such as a medical solution in fluid form, solid form, or any other suitable form, and a machine line of a medical machine configured to utilize the material to provide therapy to a patient. The connector is configured to establish the connection through the mechanical mating of a plug and a socket. The plug is configured to mechanically engage the container and the socket is configured to mechanically engage the machine line. In examples, the plug is configured to insert into a socket well defined by the socket to provide the mechanical mating. The connector includes an electromagnet configured to energize when the plug mechanically mates with the socket, in order to generate an electromagnetic force on the plug to maintain the plug mechanically mated with the socket.

In an example, a connector comprises a plug defining a channel extending between a plug inlet defined by the plug and a plug outlet defined by the plug, wherein the plug inlet is configured to mechanically engage a first conduit, and wherein the plug defines a plug armature; a socket configured to mechanically engage a second conduit, wherein the plug is configured to mechanically mate with the socket; an electromagnet configured to generate a magnetic field when the electromagnet receives an electric current; and a control circuit configured to provide the electric current to the electromagnet, wherein the plug is configured to cause the control circuit to provide the electric current to the electromagnet when the plug mechanically mates with the socket, and wherein the electromagnet is configured to cause the magnetic field to generate a magnetic force on the plug armature to help sustain the mechanical mating of the plug and the socket.

In an example, a connector comprises: a plug defining a channel extending between a plug inlet defined by the plug and a plug outlet defined by the plug, wherein the plug inlet is configured to mechanically engage a first conduit, and wherein the plug defines an armature; a socket comprising a socket body defining a socket well, wherein the socket is configured to mechanically engage with a second conduit, and wherein the plug is configured to mechanically mate with the socket when the plug translates in a first direction; an electromagnet configured to generate a magnetic field within the socket well when the electromagnet receives an electric current; and a control circuit configured to provide the electric current to the electromagnet, wherein the plug is configured to cause the control circuit to provide the electric current to the electromagnet when the plug mechanically mates with the socket, wherein the socket body is configured to form a magnetic circuit with the armature when the plug mechanically mates with the socket and the electromagnet generates the magnetic field, and wherein the electromagnet is configured to cause the electromagnetic field to generate a magnetic force on the armature in a direction toward a socket wall of the socket wall to help sustain the mechanical mating of the plug and the socket.

In an examples, a method comprises: mechanically mating a plug and a socket, wherein the plug defines a plug inlet, a plug outlet, and a channel extending between the plug inlet and the plug outlet, wherein the plug inlet is configured to mechanically engage a first conduit, and wherein the socket is configured to mechanically engage a second conduit, wherein when the plug mechanically mates with the socket, a control circuit provides an electric current to energize an electromagnet to help sustain the mechanical mating of the plug with a magnetic force generated on an armature of the plug by a magnetic field produced by the energized electromagnet; and, subsequently, removing the plug from the socket.

The details of one or more examples are set forth in the accompanying drawings and the description below. Other features, objects, and advantages will be apparent from the description and drawings, and from the claims.

DETAILED DESCRIPTION

Figure 1:
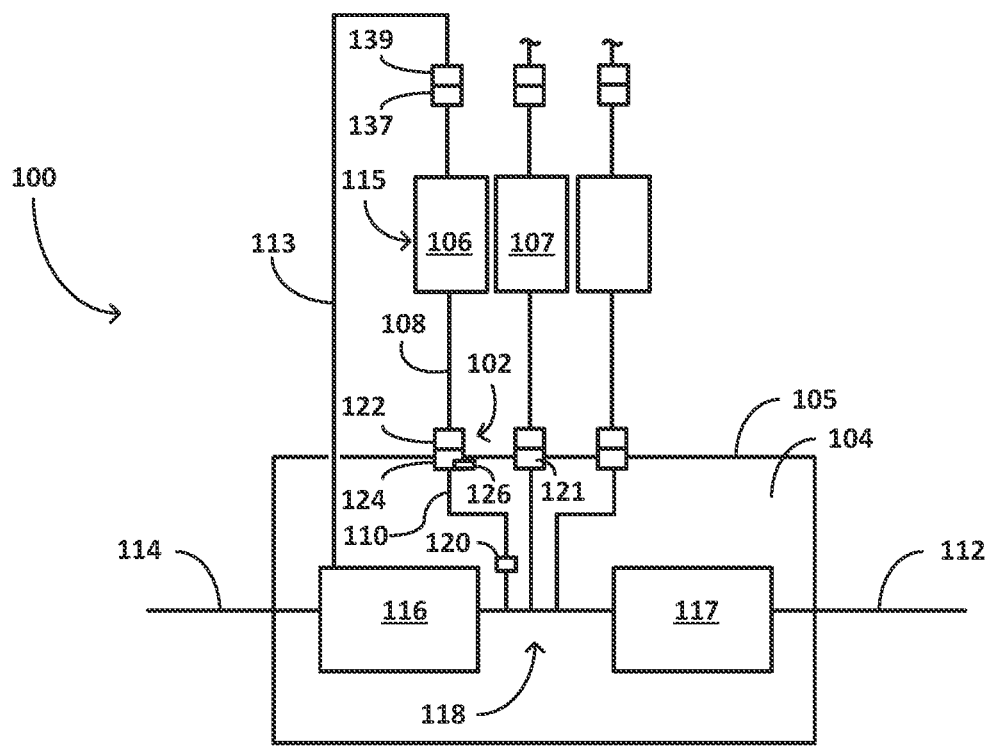
FIG. 1 is a conceptual diagram illustrating an example medical system configured to deliver a medical fluid such as dialysate.

This disclosure describes a connector configured to establish a connection between a medical machine and a container that stores material for use by the medical machine in a medical treatment of a patient. In some examples, the connector is configured to provide a connection between a materials source, such as a medical solution container (e.g., a bag) holding a medication (e.g., in a solid and/or a liquid state), and a medical machine configured to utilize the medication to provide therapy to a patient. The connector includes a plug (e.g., a bag pin) configured to mechanically mate with a socket to provide the connection. For example, the connector may be configured such that the plug inserts into the socket (e.g., by the patient, a patient caretaker, or a clinician) to mechanically mate with the socket. The connector includes an electromagnet configured to energize when the plug mechanically mates with the socket, in order to generate an electromagnetic force on the plug to maintain the plug mechanically mated with the socket. In examples, the connector provides the connection between a container containing a concentrate solution and a dialysis machine configured to utilize the concentrate solution to deliver dialysate to the patient.

The connector may be configured to substantially ensure a stable connection in systems involving pharmacological preparation and delivery to a patient. For example, the connector may be advantageous when a procedure requires the patient or another user (e.g., patient caretaker or clinician) to make a physical connections between a container, such as a disposable concentrate bag, and a medical machine, such as a dialysis machine. For example, the connector may be utilized to provide a positive indication (e.g., a light and/or audio signal) to the patient or other user that the physical connection has been established. The connector may be configured to substantially minimize or prevent inadvertent disconnections between the container and medical machine during medical treatment and/or production of a medication such as a medical solution. In some examples, the connector is configured to be used with the medical machine to provide an indication to the patient or other user that the physical connection has been lost, signaling that the medical treatment and/or production of medication is no longer occurring as intended. The connector may have particular advantages when utilized in home therapy delivery systems such as home dialysis systems where the patient or an assisting user may be required to satisfactorily perform and maintain physical connections between one or more containers and the home therapy delivery system.

The plug of the connector is configured to mechanically engage a first conduit such as a container tube connected to a medical solution container. The plug is configured to mechanically engage the first conduit to fluidly couple the first conduit and a plug inlet defined by the plug. The plug defines a channel ("plug channel") extending from the plug inlet to a plug outlet defined by the plug. The plug is configured such that, when the plug mechanically engages the first conduit, the plug establishes a flow path (e.g., for a medication such as a medical solution) from a lumen of the first conduit, through the plug channel, and to the plug outlet. The first conduit and plug channel may each be configured to establish a flow path for material in fluid or solid form.

The socket of the connector is configured to mechanically engage a second conduit, such as a line within a medical machine ("machine line"). The socket is configured to mechanically engage the second conduit to fluidly couple the plug outlet and the second conduit. The socket is configured such that, when the plug mechanically mates with the socket, the connector establishes a flow path from a lumen of the first conduit mechanically engaged by the plug to a lumen of the second conduit mechanically engaged by the socket. In some examples, a housing of a medical machine (e.g., a dialysis machine) mechanically supports the socket and the machine line. For example, the socket may be affixed to or an integral part of the housing, and the machine line may be affixed to or an integral part of the socket and/or housing. Hence, the connector may be configured such that a user (e.g., a patient, patient caretaker, or clinician) may translate the plug toward the socket to mechanically mate the plug and socket and fluidly couple a first conduit (e.g., tubing for a container) and a second conduit (e.g., a machine line within a medical machine), such that the medical machine may utilize a medication within the container to provide therapy to the patient. The second conduit may be configured to establish a flow path for material in fluid or solid form.

The connector is configured to detect the mechanical mating of plug and the socket and energize an electromagnet configured to help sustain the mechanical mating between the plug and the socket. In examples, the electromagnet is configured to minimize movements of the plug which might tend to cause an unmating of the plug and the socket. The electromagnet may be configured to substantially secure the plug in a position whereby the plug mechanically mates with the socket. In examples, the plug is configured to insert into a socket well defined by the socket to mechanically mate with the socket, and the electromagnet is configured to retain the plug within the socket well.

The connector is configured to maintain the connection between the first conduit mechanically engaged by the plug and the second conduit mechanically engaged by the socket using the electromagnet. The electromagnet is configured to generate a magnetic field when the plug mechanically mates with the socket. The plug includes an armature ("plug armature") configured to channel some portion of the magnetic field when the plug mechanically mates with the socket, such that the magnetic field causes an electromagnetic force on the plug armature to help sustain the mechanical mating. The plug armature is configured such when the magnetic field generates the electromagnetic force on the plug armature, the plug armature transfer some portion of the electromagnetic force to a body of the plug ("plug body") to help sustain the mechanical mating. In examples, the connector includes an input device configured to cause the electromagnet to cease generating the magnetic field, such that the pulling force is no longer produced and a patient or other user may unmate plug from the socket.

In examples, the socket includes a socket body defining a socket well configured to receive some portion of the plug body. The plug may be configured to substantially insert into the socket well to mechanically mate the plug and the socket. In examples, the plug is configured to insert the armature into the socket well when the plug is inserted. The electromagnet may be configured to generate the magnetic field within the socket well, such that the electromagnetic force on the armature substantially retains the plug within the socket well.

The plug is configured to cause the electromagnet to energize and produce the electromagnetic force on the plug armature when the plug mechanically mates with the socket. The plug may be configured to actuate a control circuit configured to energize the electromagnet, such that the electromagnet generates the electromagnetic force on the plug armature to help sustain the mechanical mating. For example, the plug may be configured to cause the control circuit to energize the electromagnet when the plug inserts into a socket well defined by the socket, such that the plug experiences an electromagnetic force tending to retain the plug within the socket well. In examples, the plug is configured to actuate a switch in the control circuit to cause the control circuit to provide an electric current to the windings of the electromagnet when the plug mechanically mates with the socket. In some examples, the socket includes a sliding pin configured to physically translate and close the switch, and the plug (e.g., the plug body) is configured to contact and cause translation of the sliding pin to close the switch.

The electromagnet may have any configuration sufficient to generate a magnetic field and produce an electromagnetic force on the plug armature. The electromagnet may be configured to generate an electromagnetic field producing lines of flux within the socket body. The electromagnet may include one or more windings wound around a ferromagnetic core. In examples, the electromagnet includes one or more pole pieces configured to distribute the magnetic field within the socket body. The pole pieces may extend from the core of the electromagnet. In examples, the electromagnet and/or pole pieces are configured to substantially surround and/or contact a portion of a perimeter defined by the socket body. In some examples, an inner surface of a socket wall defines the socket well, and the electromagnet and/or pole pieces substantially surround and/or contact a portion (e.g., at least 10%, at least 20%, at least 30%, at least 40%, or another percentage) of a perimeter defined by an outer surface of the socket wall opposite the inner surface.

The plug armature defined by the plug includes a ferromagnetic material such as iron that exhibits a ferromagnetic behavior when subject to the magnetic field generated by the electromagnet. The plug armature may be configured to channel some portion of the magnetic field generated by the electromagnet. In examples, the plug armature and the socket body define a portion of a magnetic circuit for the magnetic field generated by the electromagnet, such that the magnetic force generates an electromagnetic force on the plug armature tending to sustain the mechanical mating of the plug and the socket. The plug armature is configured to transfer some portion of the electromagnetic force to the plug body. In examples, the plug is configured to mechanically mate with the socket when the plug translates (or is translated by a patient or clinician) in a first direction toward the socket, and the electromagnet is configured to generate an electromagnetic force on the plug armature in the first direction, such that the electromagnetic force substantially retains the mechanical mating of the plug and the socket. Hence, the electromagnet may be configured to generate the electromagnetic force on the plug to substantially maintain a connection between a first conduit mechanically engaged with the plug (e.g., a tubing of a container) and a second conduit mechanically engaged with the socket (e.g., a machine line).

The plug body may be configured to substantially minimize a distance between the electromagnet (e.g., the pole pieces) and the plug armature in order to, for example, increase the electromagnetic force generated by the electromagnetic field and/or reduce a magnitude of the electric current supplied to the electromagnet. In examples, the plug body is configured to establish a sliding contact between a wall of the socket well and the plug armature when the socket well receives the plug. In some examples, the plug armature defines an outer periphery (e.g., a circumference) of the plug body, and the plug armature is configured to establish a sliding contact with the wall of the socket well around substantially the entirety of the outer periphery.

In some examples, the plug body is be configured such that, when the plug mechanically mates with the socket, a portion of the second conduit (e.g., an end of a machine line) inserts into the plug outlet. In examples, the socket is configured to substantially align the portion of the second conduit and the plug outlet, such that the portion of the second conduit inserts into the plug outlet when the plug mechanically mates with the socket. In examples, an inner surface defining the plug channel is configured to establish a sliding contact with an outer surface of the second conduit when the second conduit inserts into the plug outlet. In some examples, the inner surface defines a periphery (e.g., a circumference) of the plug channel, and the inner surface is configured to establish a sliding contact with the outer wall of the second conduit around substantially the entirety of the periphery of the plug channel.

In some examples, the connector is configured to assist in the proper connection of containers and the medical machine. This may help increase the success of an at-home therapies, e.g., dialysis, that require a patient or other user to make fluid connections between a material source and a medical machine by at least helping to prevent the patient (or other user) from connecting a material source to the wrong fluid line of the medical machine. Such improper connections may interfere with the success of the at-home therapy.

For example, the connector may include one or more visible indicia that helps the user align the connector for a particular container with the correct fluid line of the medical machine. As an example, a plug attached to a particular container may have a color and/or include a symbol (e.g., a graphical symbol) corresponding to a color and/or symbol of a specific socket of a medical machine. The specific socket of a connector may be configured to provide the contents of the particular container to the medical machine, such that the medical machine generates a medication using the contents of the particular container. Substantially matching the corresponding color and/or symbols of the plug and the socket may assist the patient or other user in the proper placement of the plug in the correct socket. In addition to, or instead of, the visible indicum, in some examples, a particular plug may be configured to mate with a respective socket and to not mate with other sockets of the medical machine to help a user better understand which socket a particular plug should be introduced into in order to properly connect a container fluidically connected to the plug with the medical machine.

FIG. 1 is a block diagram illustrating an example medical system 100 using an example connector 102. Medical system 100 includes a medical machine 104 configured to produce a medication (e.g., a medical solution) for a patient therapy (e.g., dialysis) using one or more concentrates. For example, medical machine 104 may be configured to produce dialysate for the patient using concentrates contained in one or more containers such as container 106. Medical system 100 may be configured to generate the medication by at least mixing a concentrate within container 106 with a fluid such as water. In examples, medical system 100 is configured to receive the fluid via fluid line 114 and deliver the medication produced (e.g., dialysate) via an infusion line 112. For example, infusion line 112 may provide dialysate to a cycler configured to provide therapy to a patient using the dialysate, or to a container configured to retain the dialysate for subsequent use.

Medical system 100 may include a conditioning system 116 configured to provide fluid received via infusion line 112 to a generation flow path 118 defined by medical machine 104. Conditioning system 116 may include, for example, a pump configured to provide a motive force to the fluid received via infusion line 112 to drive the fluid through generation flow path 118. In some examples, conditioning system 116 may include one or more filters and/or sorbent cartridges configured to remove impurities (e.g., particulate matter and/or ions) from the fluid prior to the fluid entering generation flow path 118. In addition, in some examples, conditioning system 116 may include one or more sensors, such as a conductivity sensor and/or a pressure sensor, configured to monitor a physical state or condition of the fluid prior to the fluid entering generation flow path 118. In examples, conditioning system 116 includes a degasser configured to degas the fluid prior to entering generation flow path 118. The degasser may include, for example, a vacuum pump configured to create a vacuum to remove air and other gases from the fluid prior to entering generation flow path 118.

Medical system 100 may be configured to generate a medication using the one or more concentrates held in one or more containers such as container 106 and container 107. In examples, medical system 100 may be configured to provide a fluid (e.g., purified water) to a container system 115 including container 106 such that container system 115 may generate the medical solution. For example, medical system 100 may be configured to receive a fluid via fluid line 114 and provide the fluid (e.g., from conditioning system 116) to container system 115 using a machine fluid line 113. In some examples, container system 115 may be configured to utilize a single fluid path for both an injection of fluid (e.g., purified water) into container system 115 and extraction of a medical solution. For example, container system 115 may be configured to receive the fluid via second conduit 110 and first conduit 108 in a first flow direction to generate a medical solution, and then supply the medical solution via second conduit 110 and first conduit 108 in a second flow direction opposite the first flow direction.

In examples, medical system 100 includes one or more concentrate pumps such as concentrate pump 120 configured to inject a concentrate from container 106 into generation flow path 118 via second conduit 110. In some examples, medical system 100 may include one or more additional filters (not shown) configured to filter the concentrate provided from container 106 prior to the concentrate entering generation flow path 118. The concentrate may include one or more solutes. In examples, the solute includes an osmotic agent such as glucose, dextrin, and/or icodextrin. In examples, the solute includes an ion such as sodium chloride, sodium lactate, magnesium chloride, calcium chloride, potassium chloride, and/or sodium bicarbonate.

Connector 102 is configured to fluidly couple first conduit 108 and second conduit 110, to enable medical system 100 to inject a concentrate held within container 106 into generation flow path 118. Connector 102 includes a plug 122 mechanically engaged with first conduit 108 and a socket 124 mechanically engaged with second conduit 110. Plug 122 is configured to mechanically mate with socket 124 such that a confined fluid path is established from an interior of container 106, through first conduit 108, and to second conduit 110. In examples, connector 102 defines the confined fluid path through a plug channel (not shown) defined by a body of plug 122. The plug channel may extend from a plug inlet (not shown) defined by plug 122 to a plug outlet (not shown) defined by plug 122. The plug inlet may be configured to mechanically engage first conduit 108 such that first conduit 108 is fluidically coupled with the plug outlet.

Plug 122 may be configured to mechanically mate with socket 124 such that the plug outlet is fluidically coupled to second conduit 110 when second conduit 110 is mechanically engaged by socket 124. In examples, socket 124 defines a recessed socket well, and plug 122 is configured to insert into the socket well to mechanically mate with socket 124. For example, plug 122 can have a hollow cylindrical body configured to be received in a cylindrical socket well. In some examples, socket 124 is mechanically supported by a housing 105 of medical machine 104. Hence, connector 102 may be configured to define a confined fluid path from an interior of container 106 to generation flow path 118, such that medical system 100 may generate a medication using a concentrate held in container 106 and a fluid introduced via fluid line 114.

Connector 102 is configured to substantially minimize or avoid inadvertent disconnections of plug 122 and socket 124, such that the production of medication by medical system 100 is not unintentionally interrupted. When first conduit 108 is connected to plug 122, connector 102 is configured to minimize or even prevent inadvertent disruption of the fluid connection between first conduit 108 and second conduit 110. Connector 102 includes an electromagnet 126 configured to generate a magnetic field which produces an electromagnetic force on plug 122 when plug 122 mechanically mates with socket 124. Electromagnet 126 is configured to generate the electromagnetic force on the plug armature in a direction tending to maintain the mechanical mating between plug 122 and socket 124. In examples, plug 122 is configured to mechanically mate with socket 124 when plug 122 translates (e.g., is translated by a patient or a clinician) in a first direction toward socket 124, and electromagnet 126 is configured to produce the electromagnetic force on plug 122 in a direction resisting translation of plug 122 in a direction tending to disrupt and/or degrade the mechanical mating of plug 122 and socket 124 (e.g., a direction opposite the first direction). In examples, socket 124 defines a socket well and plug 122 is configured to insert into the socket well to mechanically mate with socket 124, and electromagnet 126 is configured to produce an electromagnetic force on plug 122 in a direction tending substantially maintain plug 122 within the socket well. In some examples, electromagnet 126 is configured to produce an electromagnetic force on plug 122 in a radial direction substantially perpendicular to the first direction (e.g., perpendicular to within at least 5 degrees, at least 10 degrees, at least 20 degrees, or at least 30 degrees).

In examples, medical machine 104 may be configured to receive the particular contents of container 106 within second conduit 110 and, therefore, a particular socket such as socket 124, as opposed to another socket which may be present in medical machine 104, such as socket 121. In some examples, connector 102 is configured to help facilitate the proper connection between container 106 and a specific socket 124. For example, connector 102 can include one or more visible indicia to assist in the proper connection of specific plugs with specific sockets, such as the connection of plug 122 and socket 124. For example, plug 122 may be a component of a container system 115 including container 106, first conduit 108, and plug 122. First conduit 108 may be a flexible tube (e.g., disposable or reusable) fluidly connected to an interior of container 106. Medical machine 104 may be configured to receive the particular contents of container 106 via socket 124, in order to produce a particular medication for the treatment of a patient. Plug 122 may include a color and/or include a symbol corresponding to a color and/or symbol, respectively, of socket 124 of medical machine 104 to assist the patient or other user in the proper placement of a specific plug such as plug 122 in a specific socket such as socket 124. In examples, plug 122 is a disposable plug configured to be disposed of when one or more components of container system 115 are replaced. In examples, plug 122 is substantially affixed and/or attached to first conduit 108 and configured to be delivered to medical system 100 as part of container system 115.

Connector 102 is configured such that the mechanical mating of plug 122 and socket 124 causes electromagnet 126 to generate the electromagnetic force on plug 122. Connector 102 may include a control circuit (not shown in FIG. 1) configured to energize electromagnet 126 when plug 122 mechanically mates with socket 124, such that electromagnet 126 generates the magnetic field and produces the electromagnetic force on plug 122. In examples, plug 122 is configured to cause the control circuit to energize electromagnet 126. In some examples, the control circuit includes a switch configured to cause the control circuit to energize electromagnet 126 to produce the electromagnetic force, and plug 122 is configured to actuate the switch when plug 122 mechanically mates with socket 124.

Container system 115 may further include a fluid connector 137 configured to fluidly couple container 106 and machine fluid line 113. In examples, fluid connector 137 is configured to mechanically mate with a fluid connector 139 of machine fluid line 113 to provide the fluid coupling. In some examples, as discussed above, container system 115 may be configured to utilize a single fluid path for both an injection of fluid and extraction of medical solution. Hence, container system 115 may be a separable system configured to attach to and/or detach from medical machine 104. Fluid connector 137 and/or socket 124 may be configured such that a patient or care-giver may connect container system 115 to medical machine 104 in preparation for use of a medical solution provided by container system 115.

Medical system 100 may further include a mixing system 117 configured to provide the medication to infusion line 112. In examples, mixing system 117 includes a mixing chamber configured to further mix the concentrate from container 106 and the fluid from conditioning system 116. Mixing system 117 may include one or more sensors configured to evaluate one or more physical characteristics of the medication, such as one or more of conductivity sensors, pH sensors, pressure sensors, flow sensors, or the like. In some examples, mixing system 117 includes one or more sterilization units, such as one or more ultrafilters, microbial filters, UV light sources, or other sterilization units configured to substantially sterilize dialysate prior to infusion into a patient.

Hence, connector 102 may be configured to fluidly couple first conduit 108 and second conduit 110, such that medical system 100 may produce a medication (e.g., dialysate) using one or more concentrates delivered via first conduit 108. Connector 102 may provide the fluidic coupling using plug 122 configured to mechanically mate with socket 124. Connector 102 includes electromagnet 126 configured to energize when plug 122 mechanically mates with socket 124. Electromagnet 126 is configured to generate a magnetic field producing an electromagnetic force on plug 122 to help sustain the mechanical mating in order to, for example, substantially minimize or avoid inadvertent disconnections of plug 122 and socket 124 as medical system 100 provides a medication (e.g., dialysate).

Figure 2:
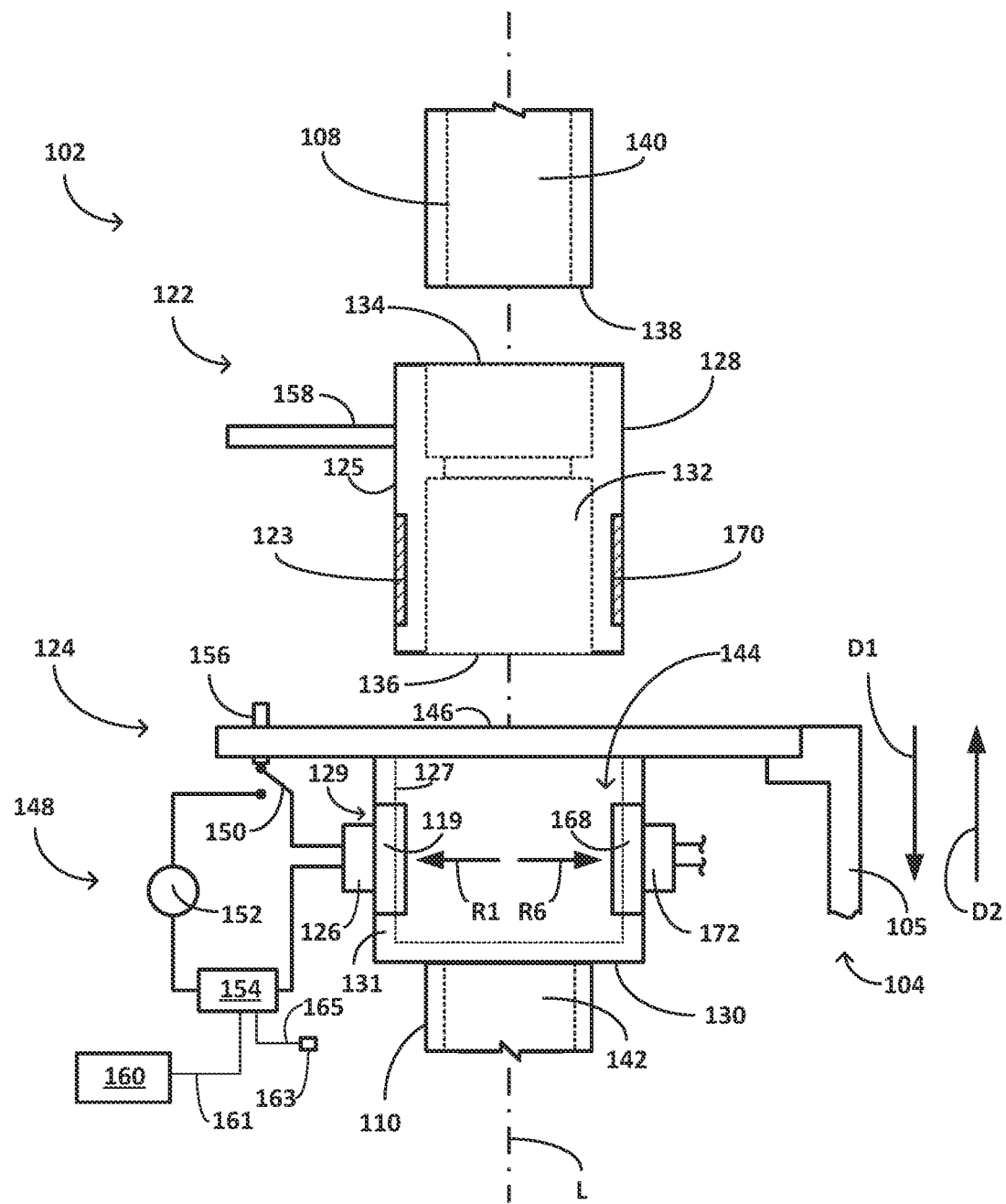
FIG. 2 is a conceptual diagram of an example connector including a plug and a socket.
Figure 3:
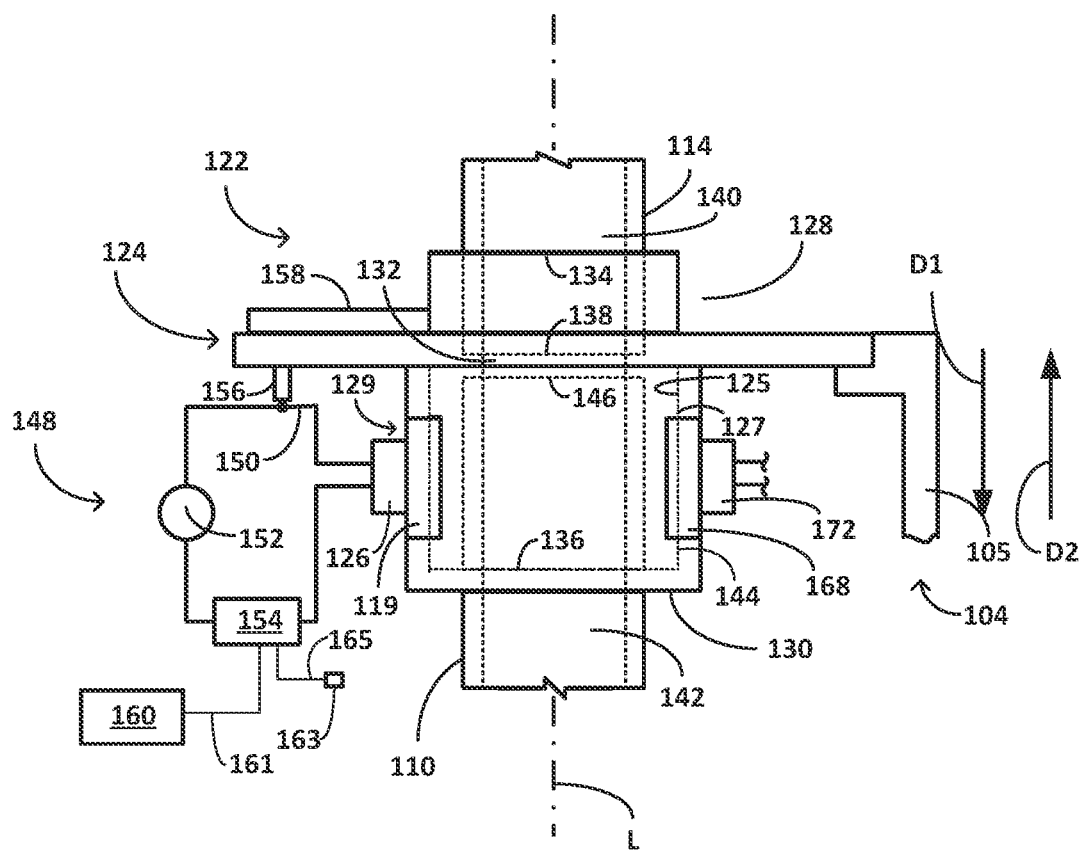
FIG. 3 is a conceptual diagram of the connector of FIG. 2 with the plug mechanically mated with the socket.
Figure 4:
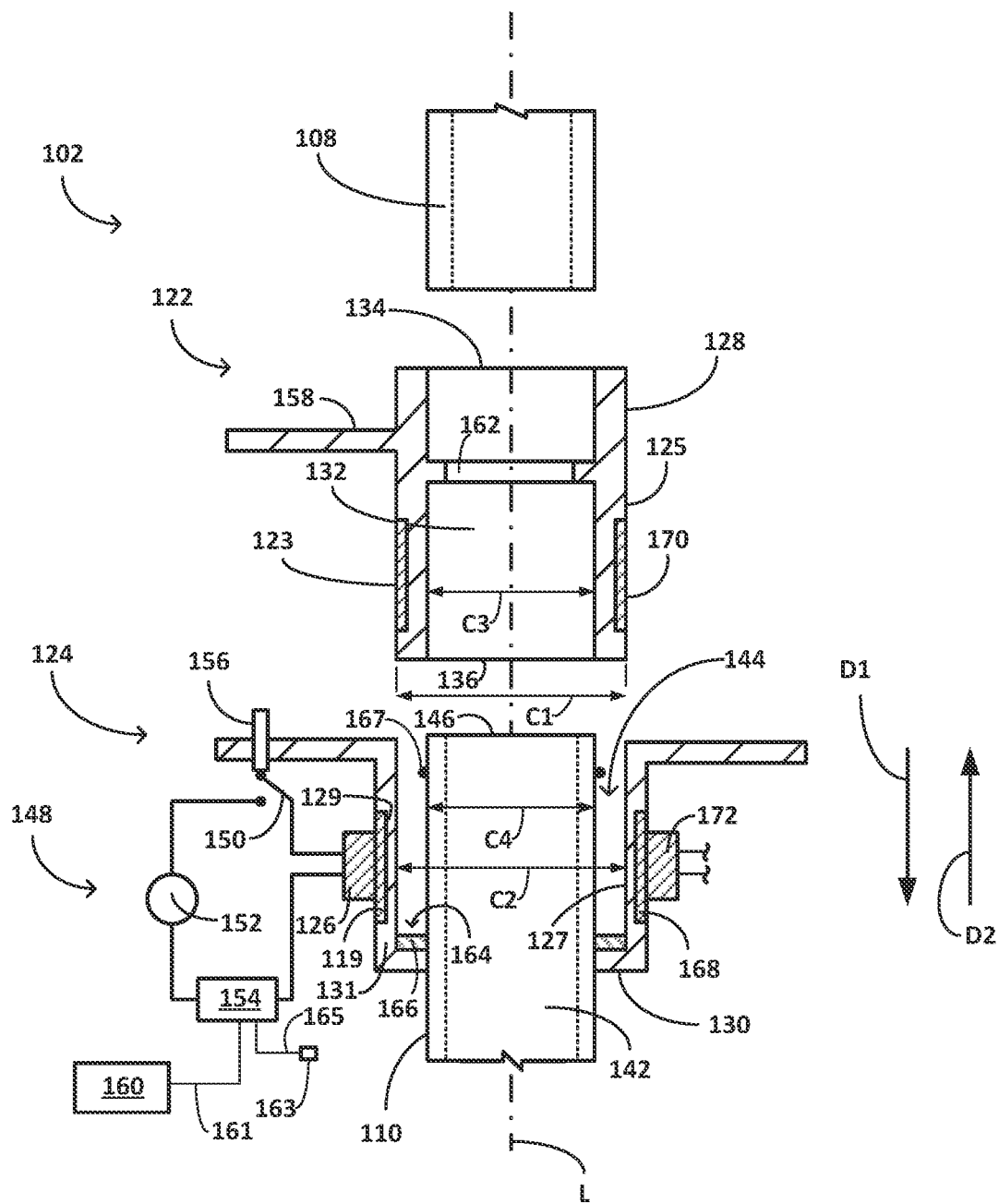
FIG. 4 is a conceptual diagram illustrating a cross-section of the connector of FIG. 2.

FIGS. 2, 3, and 4 illustrate an example connector 102 including plug 122 including plug body 128. Connector 102 further includes socket 124 including socket body 130. Plug 122 is configured to mechanically engage first conduit 108 (e.g., a bag tube from a container 106) and socket 124 is configured to mechanically engage second conduit 110 (e.g., a machine line). Plug 122 is configured to mechanically mate with socket 124 such that the first conduit 108 and the second conduit 110 are fluidly coupled. Connector 102 is configured to energize an electromagnet 126 to help sustain the mechanical mating between plug 122 and socket 124 as connector 102 provides fluid coupling between first conduit 108 and second conduit 110. Plug 122 is configured to cause electromagnet 126 to energize when plug 122 mechanically mates with socket 124, such that the energized electromagnet 126 generates a magnetic field and the magnetic field produces an electromagnetic force on a plug armature 123 of plug 122. The electromagnetic force on plug armature 123 helps to sustain the mechanical mating of plug 122 and socket 124. In examples, electromagnet 126 includes one or more pole pieces 119 configured to distribute the electromagnetic field (e.g., distribute lines of flux) generated by electromagnet 126. Pole pieces 119 may be configured to distribute the electromagnetic field over an area of an outer surface 129 defined socket 124 ("socket outer surface 129").

FIG. 3 illustrates connector 102 with plug 122 mechanically mated with socket 124 and providing fluid coupling between first conduit 108 and second conduit 110. FIG. 4 illustrates a cross-section of connector 102 with a cutting plane parallel to the page.

Plug 122 defines a channel 132 ("plug channel 132") extending through plug body 128 and opening to a plug inlet 134 and a plug outlet 136. Plug channel 132 is illustrated with dashed lines in FIGS. 2 and 3. Plug inlet 134 and plug outlet 136 are openings defined by plug body 128. Plug channel 132 is configured to establish fluid communication between plug inlet 134 and plug outlet 136. Plug 122 is configured to mechanically engage first conduit 108 to fluidly couple first conduit 108 and plug outlet 136, such that a first flow channel 140 defined by first conduit 108 may fluidly couple with plug outlet 136 through plug channel 132.

Plug 122 may be configured to mechanically engage first conduit 108 in any manner sufficient to fluidly couple first conduit 108 and plug outlet 136. In examples, plug 122 is configured to mechanically engage first conduit 108 such that plug 122 establishes a substantially confined (e.g., confined but for manufacturing tolerances) flow path from first flow channel 140 defined by first conduit 108 to plug outlet 136. In examples, plug inlet 134 is configured to receive first conduit 108 (e.g., a flexible or rigid tube). For example, plug inlet 134 can be configured to allow an end 138 of first conduit 108 ("first conduit end 138") to insert into plug channel 132 through plug inlet 134 in order to fluidly couple first conduit 108 and plug outlet 136. For example, FIG. 3 illustrates first conduit 108 inserted through plug inlet 134, such that first conduit end 138 is positioned within plug channel 132 of plug 122.

Socket 124 is configured to mechanically mate with plug 122. Socket 124 may be configured to mechanically mate with plug 122 when plug 122 is translated in a first direction D1 toward socket 124. In some examples, one of plug 122 or socket 124 defines a protrusion and the other of plug 122 or socket 124 defines a recess, and the recess is configured to receive the protrusion when socket 124 mechanically mates with plug 122. Plug 122 and socket 124 may be configured such that the mechanical mating limits movement of plug 122 relative to socket 124 at least in a direction substantially perpendicular to the first direction D1. In examples, one or more surfaces of socket 124 may be configured to substantially conform to one or more surfaces of plug 122 when socket 124 mechanically mates with plug 122. For example, a first surface 125 of plug 122 may define a complementary shape to a shape of a second surface 127 of socket 124, such that the first surface and second surface limits movement of plug 122 relative to socket 124 at least in a direction substantially perpendicular to the first direction D1. In examples, first surface 125 may be configured to contact second surface 127 when socket 124 mechanically mates with plug 122.

In an example, plug 122 defines a protrusion configured to insert into a recess of socket 124. As illustrated in FIGS. 2, 3, and 4, socket 124 may be configured such that socket body 130 defines a socket well 144 recessed into socket body 130. Socket well 144 may be configured such that plug 122 (e.g., a portion of plug body 128) inserts into socket well 144 to mechanically mate with socket 124. In examples, plug body 128 is configured to establish a sliding contact with second surface 127 defining a wall of socket well 144 and first surface 125 of plug 122 when plug 122 inserts into socket well 144. In some examples, first surface 125 defines an outer periphery (e.g., a circumference) of the plug 122 and second surface 127 defines an inner periphery of socket well 144, and first surface 125 is configured to establish a sliding contact with second surface 127 around substantially the entirety of the outer periphery and the inner periphery.

Socket 124 is configured to mechanically engage second conduit 110. Second conduit 110 may be, for example, a machine line of medical machine 104. In examples, socket 124 is configured to mechanically engage second conduit 110 such that, when plug 122 mechanically mates with socket 124, plug channel 132 fluidly couples with second conduit 110. Socket 124 may be configured such that the mechanical mating of plug 122 and socket 124 establishes a substantially confined flow path from plug channel 132 to a second flow channel 142 defined by second conduit 110. Hence, connector 102 may be configured to form a physical connection between first conduit 108 (e.g., tubing for a container 106 (FIG. 1)) and second conduit 110 (e.g., a machine line for medical machine 104 (FIG. 1)) when plug 122 mechanically mates with socket 124. In examples, housing 105 of medical machine 104 mechanically supports socket 124 and/or second conduit 110. In examples, socket 124 may be affixed to or an integral part of medical machine 104 and/or housing 105. Second conduit 110 may be affixed to or an integral part of socket 124, medical machine 104, and/or housing 105.

Socket 124 may be configured to mechanically engage second conduit 110 in any manner sufficient to fluidly couple plug channel 132 with second conduit 110 when plug 122 mechanically mates with socket 124. In examples, socket 124 is configured to mechanically engage second conduit 110 such that plug 122 establishes a substantially confined flow path from plug channel 132 to second flow channel 142 of second conduit 110. Socket 124 may be configured to mechanically engage second conduit 110 such that plug 122 establishes a substantially confined flow path from first flow channel 140 of first conduit 108 to second flow channel 142 of second conduit 110. In examples, socket 124 is configured to mechanically engage second conduit 110 such that an end 146 of second conduit 110 ("second conduit end 146") inserts into plug channel 132 through plug outlet 136 when plug 122 mechanically mates with socket 124. For example, FIG. 3 illustrates second conduit 110 inserted through plug outlet 136, such that second conduit end 146 is positioned within plug channel 132 of plug 122.

Electromagnet 126 is configured to energize and generate an electromagnetic force on plug 122 when plug 122 mechanically mates with socket 124. Electromagnet 126 is configured to generate a magnetic field which interacts with plug armature 123 when plug 122 mechanically mates with socket 124. Electromagnet 126 is configured such that the magnetic field interaction causes a ferromagnetic response in plug armature 123 and generates the electromagnetic force on plug armature 123 in a direction tending to sustain the mechanical mating of plug 122 and socket 124. Plug armature 123 is configured to transmit at least a portion of the electromagnetic force to plug 122. In examples, electromagnet 126 is configured to minimize movements of plug 122 relative to socket 124 which tend to cause plug 122 to unmate (e.g., break the mechanical mating) with socket 124 and break the connection between fluid lines 108, 110 (FIG. 1). Thus, electromagnet 126 may be configured to substantially secure plug 122 in a position whereby plug 122 mechanically mates with socket 124. In examples, plug 122 is configured to mechanically mate with socket 124 when plug 122 translates in the first direction D1 toward socket 124, and electromagnet 126 is configured to produce the electromagnetic force on plug 122 in a resisting translation of plug 122 in a second direction D2 substantially opposite the direction D1, in order to help sustain the mechanical mating of plug 122 and socket 124. In examples, electromagnet 126 is configured to produce the electromagnetic force on plug 122 in a radial direction R1 substantially perpendicular to first direction D1 and/or second direction D2. In examples, plug 122 is configured to unmate (e.g., break the mechanical mating) with socket 124 when plug 122 translates in a second direction D2 opposite the first direction D1.

Electromagnet 126 may have any configuration sufficient to produce the electromagnetic force on plug armature 123 when plug 122 mechanically mates with socket 124. In examples, electromagnet 126 is configured to generate a magnetic field producing a magnetic flux through an area defined by socket 124, such as an area defined by socket well 144. For example, electromagnet 126 is configured to generate a magnetic flux through an area defined by second surface 127. Electromagnet 126 may at least partially surround some portion of socket body 130.

Electromagnet 126 may include one or more pole pieces such as pole piece 119 configured to distribute a magnetic field generated by electromagnet 126 within socket body 130. Pole piece 119 may extend from a core of electromagnet 126. In examples, pole piece 119 is configured to substantially surround and/or contact a portion of a perimeter defined by socket outer surface 129. In examples, pole piece 119 is configured to cause the electromagnetic field (e.g., lines of flux) generated by electromagnet 126 to pass into a socket wall 131 defining a boundary of socket well 144. Pole piece 119 may be configured to cause the electromagnetic field to pass into plug armature 123 of plug 122 when plug 122 mechanically mates with socket 124. Pole piece 119 may substantially surround and/or contact any portion or substantially all of a perimeter defined by socket outer surface 129. In examples, pole piece 119 substantially surrounds and/or contacts least 10%, at least 20%, or at least 30% of the perimeter defined by an outer surface of the socket wall.

In examples, socket 124 defines a central axis L passing through socket well 144. Socket 124 may be configured such that central axis L passes through second flow channel 142 when socket 124 mechanically supports second fluid conduit 110. Pole piece 119 may be configured such that the radial direction R1 of the electromagnetic force on plug armature 123 extends in a direction from a central axis L and toward second surface 127. Pole piece 119 may be configured such that the radial direction R1 is substantially perpendicular to second surface 127 (e.g., perpendicular to within at least 5 degrees, at least 10 degrees, at least 20 degrees, or at least 30 degrees). In examples, pole piece 119 is configured such that, when plug 122 mechanically mates with socket 124 and electromagnet 126 generates the magnetic field, a magnetic force is exerted on plug armature 123 in a direction toward second surface 127. The electromagnetic force acting on plug armature 123 in the direction R1 may be a force in a force distribution acting on armature 123.

Figure 5:
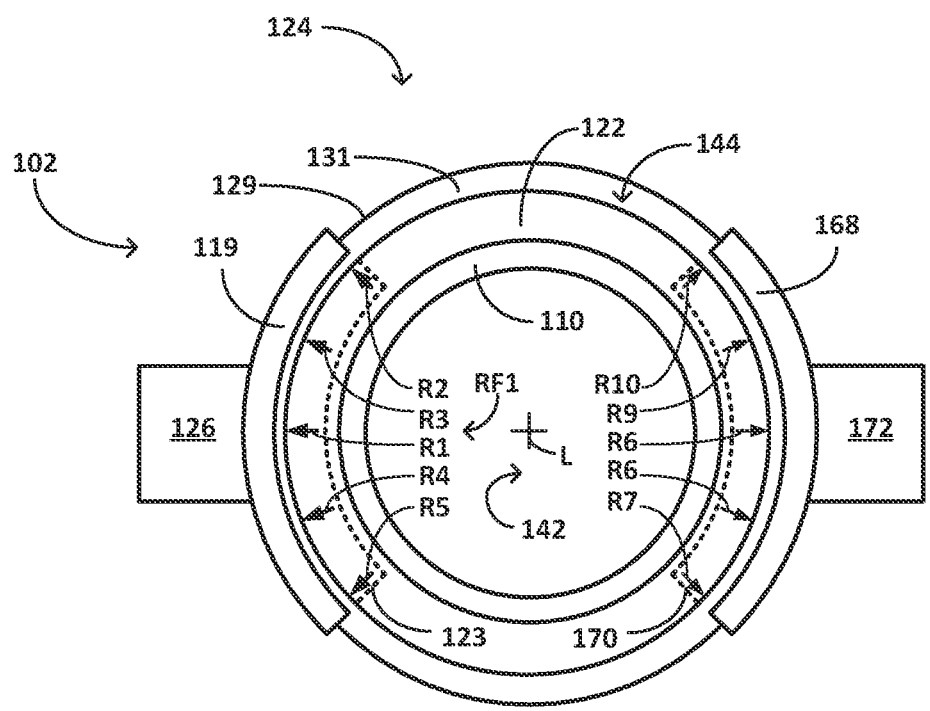
FIG. 5 is a conceptual diagram of an example plug inserted within a socket.

As an example, FIG. 5 illustrates connector 102 with plug 122 mechanically mated with socket 124. Plug 122 is inserted within socket well 144 of socket 124. Socket 124 mechanically supports second conduit 110 defining second flow channel 142 surrounding central axis L. Central axis L is perpendicular to the page. Pole piece 119 of electromagnet 126 extends at least partially around a portion of socket outer surface 129 defined by socket wall 131. Plug armature 123 of plug 122 is illustrated with dashed lines. Pole piece 119 may be configured to distribute an electromagnetic field generated by electromagnet 126 over an area defined by socket outer surface 129 such that the electromagnetic force generates a force distribution RF1 (e.g., R1, R2, R3, R4, and R5) acting on plug armature 123 in a direction toward second surface 127 of socket wall 131. In examples, pole piece 119, socket wall 131, and plug armature 123 are configured to form a magnetic circuit when electromagnet 126 generates the magnetic field.

Connector 102 may include any number of pole pieces arranged in any manner to distribute an electromagnetic field within socket 124 (e.g., to distribute over a socket outer surface 129). In examples, connector 102 includes at least a second pole piece 168 configured to distribute an electromagnetic field over a second portion of socket 124 (e.g., over a second area of socket outer surface 129). Second pole piece 168 may be configured similarly to pole piece 119. Pole piece 168 may be configured to distribute an electromagnetic field over an area defined by socket outer surface 129.

Plug 122 may include any number of armatures configured to transfer some portion of an electromagnetic force to plug 122 (e.g., plug body 128). In examples, plug 122 includes at least a second plug armature 170 configured to transfer an electromagnetic force to plug 122. Second plug armature 170 may be configured similarly to armature 123. Pole piece 168 and/or pole piece 119 may be configured to distribute an electric field over an area defined by socket outer surface 129 such that the electromagnetic force generates a second force distribution RF2 (e.g., R6, R7, R8, R9, and R10) acting on second plug armature 170 in a direction toward second surface 127 of socket wall 131. In examples, the plug armature 123 is configured such that the second force RF2 includes one or more forces (e.g., R6) acting in a direction substantially opposite a direction of one or more forces (e.g., R1) of the force distribution RF1. In examples, pole piece 168, socket wall 131, and second plug armature 170 are configured to form a magnetic circuit when electromagnet 126 or another electromagnet (e.g., electromagnet 172) generates a magnetic field. Hence, connector 102 may include one or more pole pieces (e.g., pole piece 119 and pole piece 168) configured to generate one or more force distributions exerted on plug 122 in a direction toward socket 131.

Connector 102 may include any number of electromagnets configured to generate an electromagnetic force on plug 122. In examples, connector 102 includes second electromagnet 172 configured to generate an electromagnetic force (and/or force distribution) on plug 122. Each electromagnet may include one or more pole pieces forming a magnetic circuit with one or more armatures of plug 122 when the electromagnet generates an electromagnetic field. In some examples, a first electromagnet (e.g., electromagnet 126) includes a first pole piece (e.g., pole piece 119) and a second electromagnet (e.g., electromagnet 172) includes a second pole piece (e.g., pole piece 168) different from the first pole piece. In some examples, a first armature (e.g., armature 123) forms a first magnetic circuit with a first pole piece (e.g., pole piece 119) and a second armature (e.g., second plug armature 170) forms a second magnetic circuit with a second pole piece (e.g., pole piece 168) different from the first pole piece.

Connector 102 includes a control circuit 148 configured to provide an electric current to electromagnet 126, 172. In examples, electromagnet 126, 172 includes one or more windings configured to produce the magnetic field, and control circuit 148 is configured to provide the electric current to the one or more windings. Control circuit 148 is configured to provide the electric current to cause electromagnet 126, 172 to generate the magnetic field. Control circuit 148 may include a power supply 152 configured to provide electrical power to control circuit 148. In examples, control circuit 148 includes circuitry 154 electrically connected to power supply 152. Circuitry 154 may be configured to receive electrical power from power supply 152 and provide an electric current to electromagnet 126, 172. For example, circuitry 154 may be a current source configured to generate an output current using electrical power from power supply 152, with circuitry 154 configured to provide the output current to electromagnet 126, 172. Circuitry 154 may be a voltage source configured to generate an output voltage using electrical power from power supply 152, with circuitry 154 configured to apply the output voltage to electromagnet 126, 172 (e.g., across one or more windings of electromagnet 126, 172) to provide the electric current to electromagnet 126, 172. Power supply 152 may be substantially dedicated to control circuit 148, or may also provide power to other components and/or systems, such as other components and/or systems of connector 102 and/or medical machine 104.

Plug 122 is configured to actuate control circuit 148 to cause control circuit 148 to provide the electric current to electromagnet 126, 172, such that electromagnet 126, 172 energizes and produces the electromagnetic force on plug armature 123, 170 when plug 122 mechanically mates with socket 124. In some examples, plug 122 is configured to actuate a switch 150 of control circuit 148 when plug 122 mechanically mates with socket 124; such actuation of switch 150 causes control circuit 148 to provide the electric current to electromagnet 126, 172. Switch 150 may be configured to cause control circuit 148 to provide the electric current to electromagnet 126, 172 when switch 150 is actuated (e.g., in a closed position). Switch 150 may be any type of switch configured to actuate when plug 122 mechanically mates with socket 124, including a microswitch (e.g., a miniature snap-action switch), an electromechanical switch, a mechanical switch, a reed switches, a limit switch, or another type of switch configured to detect a proximity of plug 122 to socket 124. Switch 150 may be configured to detect the proximity of plug 122 to socket 124 in any manner, including contact with plug 122 or a component displaced by plug 122, a potentiometer position sensor, a linear variable differential transformer/voltage displacement (LVDT) transducer, a hall-effect magnetic sensor, a mechanical counter, a cam, an actuating arm, and the like.

In examples, socket 124 includes a pin 156 configured to actuate (e.g., close) switch 150 when pin 156 translates (e.g., in the direction D1). In some examples, pin 156 is a sliding pin configured to slidably translate (e.g., in direction D1) to actuate switch 150. In examples, plug 122 includes a skirt 158 extending from plug body 128, with skirt 158 configured to contact and translate sliding pin 156 when plug 122 mechanically mates with socket 124. As illustrated in FIG. 3, skirt 158 may cause pin 156 to translate and act to close switch 150, such that control circuit 148 provides an electric current to electromagnet 126, 172. For example, skirt 158 may be configured such that, when plug 122 translates in the direction D1 to mechanically mate with socket 124, skirt 158 contacts and causes a translation of pin 156 in the direction D1, causing pin 156 to actuate switch 150. In examples, pin 156 is mechanically supported by socket body 130 and configured to slidably translate relative to a portion of socket body 130.

In examples, control circuit 148 is configured to de-actuate and cease sending an electric current to electromagnet 126, 172 when plug 122 and socket 124 are mechanically unmated. Switch 150 may be configured to de-actuate (e.g., open) when plug 122 is unmated from socket 124, such that electromagnet 126, 172 ceases generating a magnetic field and producing the electromagnetic force on plug armature 123, 170. For example, switch 150 may include an elastic element configured to compress and/or deform when skirt 158 translates pin 156 to actuate switch 150 and cause electromagnet 126, 172 to generate the magnetic field. In examples, switch 150 includes an elastic cantilever configured to elastically deform when switch 150 actuates. For example, the elastic cantilever may be resiliently biased to place switch 150 in a de-actuated condition. Pin 156 may be configured to exert a force on the elastic cantilever to overcome the resilient biasing and place switch 150 in an actuated position. The elastic cantilever may be configured such that switch 150 de-actuates when plug 122 is mechanically uncoupled from socket 124 (e.g., when pin 156 ceases exerting the force). Electromagnet 126, 172 may be configured to generate an electromagnetic force on plug armature 123, 170 sufficient to maintain the elastic element in a compressed and/or deformed condition. In some examples, switch 150 is a proximity switch configured to de-actuate and secure the electric current from control circuit 148 when plug 122 is displaced from socket 124. Switch 150 may be configured to detect the displacement of plug 122 from socket 124 in any manner, contact with a component displaced by plug 122, a potentiometer position sensor, a linear variable differential transformer/voltage displacement (LVDT) transducer, a hall-effect magnetic sensor, a mechanical counter, a cam, an actuating arm, and the like.

In some examples, pin 156 includes a pin elastic element configured to compress and/or deform when skirt 158 translates pin 156. The pin elastic element may be configured to expand to exert a force on pin 156 which tends to separate pin 156 and switch 150, such that when skirt 158 is not in contact with pin 156 (e.g., when plug 122 is uncoupled with socket 124), the elastic element translates pin 156 in a direction away from switch 150, such that pin 156 may substantially re-set into an initial position when skirt 158 is not in contact with pin 156. Electromagnet 126, 172 may be configured to generate a magnetic force on plug 122 sufficient to maintain the pin elastic element in a compressed and/or deformed condition.

In examples, connector 102 includes an output device 163 configured to provide an output to a patient or other user when plug 122 mechanically mates with socket 124. This output may provide a positive indication to the user that container 106 is properly connected to medical machine 104. The output provided by the output device 163 may be, for example, a light, a sound, or some other output discernable by the patient or other user. In some examples, output device 163 is configured to provide the output when control circuit 148 is energized (e.g., when switch 150 is actuated by plug 122). In some examples, circuitry 154 is configured to detect when control circuit 148 is energized and cause output device 163 to provide the output. Circuitry 154 may cause output device 163 to provide the output. Output device 163 may be any device configured to provide an output discernable by the patient or other user. In some examples, output device 163 is mechanically supported by housing 105 of medical machine 104. In other examples, output device 163 is an external device such as a smart phone, tablet, or other processing device configured to receive a communication from circuitry 154 via, for example, communication link 165.

In examples, output device 163 and/or control circuit 148 (e.g., circuitry 154) may be configured to provide an output to a control components and/or circuitry within medical machine 104 (FIG. 1) when plug 122 mechanically mates with socket 124. The control components and/or circuitry may be configured to use the output to control an operation of medical machine 104. For example, the control components and/or circuitry may use the output to determine if a medical treatment cycle enabled by medical machine 104 may commence and/or continue.

In examples, connector 102 includes an input device 160 configured to cause control circuit 148 to cease providing the electric current to electromagnet 126, 172. Input device 160 may be configured to receive a user input and provide the user input to control circuit 148 via, for example, communication link 161. Control circuit 148 may be configured to cease providing the electric current to electromagnet 126, 172 in response to the user input. In examples, circuitry 154 is configured to receive the user input from input device 160 and cease providing the electric current to electromagnet 126, 172. In some examples, control circuit 148 may be configured to cease providing the electric current to electromagnet 126, 172 using switch 150. For example, control circuit 148 may be configured to de-actuate switch 150 in response to the user input received from input device 160.

Plug 122 and socket 124 may be configured to define at least a portion of a magnetic circuit when plug 122 mechanically mates with socket 124 and electromagnet 126, 172 generates a magnetic field. Connector 102 may be configured to cause some portion of plug 122 (e.g., plug armature 123, 170) and socket 124 (e.g., socket body 130) to form a relatively low reluctance path for the magnetic field generated by electromagnet 126, 172 when plug 122 mechanically mates with socket 124. Plug armature 123, 170 and socket body 130 may be configured to channel some portion of the magnetic field generated by electromagnet 126, 172 to cause the magnetic field to follow a path defined by plug armature 123, 170 and socket body 130. Plug armature 123, 170 and socket body 130 may be configured such that the magnetic field generated by electromagnetic 126, 172 exerts the electromagnetic force on plug armature 123, 170 tending to cause plug 122 to move to and/or remain within a flux of the magnetic field. In examples, electromagnet 126, 172 and/or pole pieces 119, 168 are configured to generate a higher magnetic flux within socket well 144 compared to a magnetic flux generated outside of socket well 144, such that the magnetic field generates the electromagnetic force on plug armature 123, 170 tending to cause plug 122 to move to and/or remain within socket well 144.

In examples, plug 122 is configured to establish a sliding fit with socket 124 to minimize and/or reduce a magnetic reluctance between plug armature 123, 170 and socket body 130 when plug 122 mechanically mates with socket 124. Minimizing and/or reducing the magnetic reluctance between plug armature 123, 170 and socket body 130 may reduce the current requirements on control circuit 148 required to cause electromagnet 126, 172 to generate a magnetic field sufficient to generate the electromagnetic force on plug armature 123, 170. As an example, connector 102 may be configured such that first surface 125 of plug 122 establishes a sliding fit with second surface 127 of socket 124 to, for example, minimize and/or reduce a magnetic reluctance between plug armature 123, 170 and socket body 130 when plug 122 mechanically mates with socket 124.

In some examples, plug armature 123, 170 substantially surrounds (e.g., extends around at least 10%, at least 20%, at least 30%, at least 40%, or another percentage of a periphery of plug 122. Plug armature 123, 170 may be configured to establish a sliding fit around a periphery defined by socket body 130 when plug 122 mechanically mates with socket 124. In some examples, plug 122 defines a cylindrical shape and plug armature 123, 170 substantially extends around a circumferential periphery of the cylindrical shape. Plug armature 123, 170 may be configured to establish the sliding fit around an inner periphery of socket well 144 when plug 122 mechanically mates with socket 124.

In some examples, medical machine 104 includes a plurality of sockets such as socket 124 and socket 121 (FIG. 1). Connector 102 may be configured such that plug 122 is configured to mechanically mate with only one or more specific sockets mechanically supported by medical machine 104. For example, connector 102 may be configured to allow plug 122 to mechanically mate with socket 124 while substantially limiting and/or preventing plug 122 from mechanically mating with a different socket, such as socket 121 (FIG. 1). Limiting the sockets with which plug 122 may mechanically mate may limit and/or avoid misconnection of container 106 to a machine line mechanically supported by a socket other than socket 124.

In examples, and referring to FIG. 4, plug 122 defines an outer cross-sectional dimension C1 (e.g., a diameter) and socket well 144 defines an inner cross-sectional dimension C2 (e.g., a diameter). Plug 122 may be configured such that outer dimension C1 allows plug 122 to insert into socket well 144 having inner dimension C2 when plug 122 mechanically mates with socket 124. For example, plug 122 may be configured such that outer dimension C1 causes a plug 122 to establish a sliding fit with socket well 144 having inner dimension C2 when plug 122 mechanically mates with socket 124. Medical machine 104 may be configured such that a different socket such as socket 121 (FIG. 1) defines an inner cross-sectional dimension less than or greater than inner dimension C2, such that plug 122 is substantially prevented from mechanically mating with socket 121. For example, the inner dimension of socket 121 may be less than outer dimension C1 of plug 122, such that plug 122 is substantially prevented from inserting into socket 121. The inner dimension of socket 121 may be greater than outer dimension C1 of plug 122 such that plug 122 is substantially prevented from establishing a sliding fit with socket 121. Outer dimension C1 may be a diameter defined by plug 122 and inner dimension C2 may be a diameter defined by socket 124.

In examples, plug channel 132 defines an inner cross-sectional dimension C3 and socket 124 is configured to mechanically support a second conduit 110 defining an outer dimension C4. Plug channel 132 may be configured such that inner dimension C3 allows second conduit end 146 of second conduit 110 having outer dimension C4 to insert through plug outlet 136 and into plug channel 132 when plug 122 mechanically mates with socket 124 (as indicated in FIG. 3). In examples, plug channel 132 is configured such inner dimension C3 causes plug channel 132 to establish a sliding fit with second conduit 110 mechanically engaged by socket 124 when plug 122 mechanically mates with socket 124. In some examples, to help a user align plug 122 with the intended socket, medical machine 104 may be configured such that a different socket such as socket 121 (FIG. 1) is configured to support a machine line defining a different outer cross-sectional dimension less than or greater than C3, such that plug channel 132 is substantially prevented from mechanically mating with socket 121. For example, socket 121 may be configured to mechanically engage a machine line having an outer cross-sectional dimension greater than inner dimension C3 of plug channel 132, such that plug channel 132 is substantially prevented from receiving the machine line via plug outlet 136. The outer cross-sectional dimension of the machine line may be less than inner dimension C3 of plug channel 132, such that plug channel 132 is substantially prevented from establishing a sliding fit with the machine line. Inner dimension C3 may be a diameter defined by plug channel 132 and outer diameter dimension C4 may be a diameter defined by second conduit 110.

In some examples, plug 122 defines a stop 162 configured to protrude into plug channel 132. Stop 162 may be configured to contact second conduit end 146 when plug channel 132 receives second conduit 110 via plug outlet 136. In examples, plug 122 is configured such that stop 162 contacts second conduit end 146 substantially when plug body 128 contacts a seat 164 defined by socket 124. Seat 164 may include a portion of socket 124 configured to mechanically engage second conduit 110. In some examples, seat 164 comprises a hydraulic sealing system 166 (e.g., an O-ring) or another fluid seal configured to contact plug body 128 when plug body contacts seat 164. Hydraulic sealing system 166 may comprises a compressible material configured to, for example, compress when contacted by plug body 128, such that plug body 128 and seat 164 contact to form a substantially fluidically sealed contact (e.g., completely fluid sealed or nearly completely fluid sealed to the extent permitted by manufacturing tolerances). In some examples, instead of or in addition to hydraulic sealing system 166, plug body 128 (e.g., an inner surface defining plug channel 132) is configured to contact a sealing system 167 (FIG. 4) to form a substantially fluidically sealed contact with second fluid conduit 110 when plug body 128 mechanically engages second fluid conduit 110. In examples, sealing system 167 is an O-ring substantially surrounding a portion of second fluid conduit 110 within socket well 144.

In some examples, plug 122 is configured to limit and/or prevent the mechanical mating of plug 122 with another socket defined by medical machine 104, such as socket 121 (FIG. 1). For example, plug 122 can define stop 162 that is configured to contact a conduit end of a machine line mechanically engaged with socket 121 (which is not intended to receive plug 122) and prevent skirt 158 from actuating a switch configured to energize an electromagnet associated with socket 121. Hence, plug 122 may define stop 162 such that plug 122 is prevented from energizing the electromagnet associated with socket 121, such that the electromagnet associated with socket 121 is prevented from generating a pulling force on plug armature 123, 170 of plug 122. In some examples, medical machine 104 may be configured to define individual sockets such as socket 124 and socket 121 such that only a specifically configured plug may energize an electromagnet associated with an individual socket to cause the electromagnet to generate an electromagnetic force on a plug armature of the specifically configured plug. Visible indicia defined by one or more plugs and matching a respective socket may be used alone in combination with stop 162 to help a user align a plug with the proper socket.

Control circuit 148 and/or circuitry 154, as well as other control circuitry described herein, can comprise any suitable arrangement of hardware, software, firmware, or any combination thereof, to perform the techniques attributed to connector 102 herein. For example, control circuit 148 and/or circuitry 154 may include any one or more microprocessors, digital signal processors (DSPs), application specific integrated circuits (ASICs), field programmable gate arrays (FPGAs), or any other equivalent integrated or discrete logic circuitry, as well as any combinations of such components.

Communication links 161, 165, as well as other communication links described herein, may be hard-line and/or wireless communications links. In some examples, communication links 161, 165 may comprise some portion of control circuit 148 and/or circuitry 154. Communication links 161, 165 may comprise a wired connection, a wireless Internet connection, a direct wireless connection such as wireless LAN, Bluetooth™, Wi-Fi™, and/or an infrared connection. Communication links 161, 165 may utilize any wireless or remote communication protocol.

Figure 6:
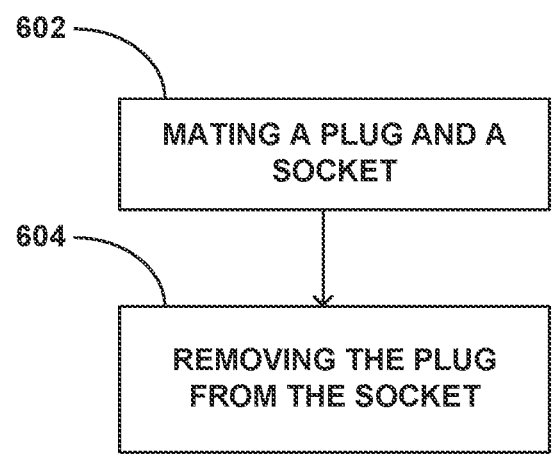
FIG. 6 is a flow diagram of an example technique of using the connector.

An example technique for connecting a container with medical machine 104 is illustrated in FIG. 6. Although the technique is described mainly with reference to connector 102 of FIGS. 1-5, the technique may be applied to other connectors and in other examples.

The technique includes mechanically mating plug 122 and socket 124 (602). Plug 122 defines plug inlet 134, plug outlet 136, and plug channel 132. Plug inlet 134 is configured to mechanically engage a first conduit 108. Socket 124 is configured to mechanically engage a second conduit 110. In an example, one of plug 122 or socket 124 defines a protrusion and the other of plug 122 or socket 124 defines a recess, and the recess receives the protrusion when socket 124 mechanically mates with plug 122. In examples, first surface 125 of plug 122 contacts second surface 127 of socket 124 when socket 124 mechanically mates with plug 122. Plug 122 may define a protrusion configured to insert into socket well 144 defined by socket 124. Plug body 128 may contact seat 164 of socket 124 when plug 122 mechanically mates with socket 124. In examples, socket 124 may be configured to mechanically mate with plug 122 when plug 122 is translated in the first direction D1 toward socket 124. Plug 122 and socket 124 may be configured such that the mechanical mating between plug 122 and socket 124 limits movement of plug 122 relative to socket 124 at least in a direction substantially perpendicular to the first direction D1.

As discussed above, plug 122 is configured to cause control circuit 148 to provide an electric current to energize electromagnet 126, 172 when plug 122 mechanically mates with socket 124. For example, electromagnet 126, 172 is configured to produce a magnetic field generating an electromagnetic force on plug armature 123, 170 when control circuit 148 provides the electric current. In examples, the electromagnetic force acts on plug armature 123, 170 in the first direction D1. In examples, plug 122 actuates switch 150 of control circuit 148 when plug 122 mechanically mates with socket 124 to cause control circuit 148 to provide the electric current. Switch 150 may be configured to detect a proximity of plug 122 to socket 124 in any manner. In examples, plug 122 translates a pin 156 configured to actuate switch 150 when plug 122 mechanically mates with socket 124. In examples, plug 122 includes skirt 158 extending from plug body 128. Skirt 158 may be configured to contact and translate sliding pin 156 when plug 122 mechanically mates with socket 124. In examples, pin 156 is mechanically supported by socket body 130 and configured to slidably translate relative to a portion of socket body 130. Control circuit 148 is configured to cause output device 163 to provide an output to a patient or another user when plug 122 mechanically mates with socket 124.

Plug 122 and socket 124 may define a portion of a magnetic circuit when plug 122 mechanically mates with socket 124 and electromagnet 126, 172 generates a magnetic field. Plug armature 123, 170 and socket body 130 may channel some portion of the magnetic field generated by electromagnet 126, 172 to cause the magnetic field to follow a path defined by plug armature 123, 170 and socket body 130 when electromagnet 126, 172 generates the magnetic field. Electromagnet 126, 172 may be configured to cause the magnetic field to exert the electromagnetic force on plug armature 123, 170 in a direction tending to cause plug 122 to move to and/or remain within a flux of the magnetic field. In examples, electromagnet 126, 172 generates a higher magnetic flux within socket well 144 compared to a magnetic flux generated outside of socket well 144 when electromagnet 126, 172 generates the magnetic field, such that the magnetic field generates the electromagnetic force on plug armature 123, 170 tending to cause plug 122 to move to and/or remain within socket well 144.

Plug 122 may establish a sliding fit with socket 124 when plug 122 mechanically mates with socket 124. In examples, first surface 125 of plug 122 establishes a sliding fit with second surface 127 of socket 124 when plug 122 mechanically mates with socket 124. In examples, plug body 128 establishes a sliding fit around an periphery defined by socket body 130 when plug 122 mechanically mates with socket 124. In examples, plug 122 defines a cylindrical shape and plug armature 123, 170 substantially extends around a circumferential periphery of the cylindrical shape. Plug armature 123, 170 may be configured to establish the sliding fit around an inner periphery of socket well 144 when plug 122 mechanically mates with socket 124.

Plug 122 may form a connection between first conduit 108 mechanically engaged with plug inlet 134 and second conduit 110 mechanically supported by socket 124 when plug 122 mechanically mates with socket 124. In examples, plug channel 132 is configured to receive second conduit 110 via plug outlet 136 when plug 122 mechanically mates with socket 124. Plug 122 may include a stop 162 protruding into plug channel 132 and configured to contact second conduit end 146 when plug channel 132 receives second conduit 110. In examples, plug body 128 is configured to contact seat 164 of socket 124 when plug 122 mechanically mates with socket 124. Plug 122 may be configured such that stop 162 contacts second conduit end 146 when plug body 128 contacts seat 164. In examples, seat 164 comprises a compressible material such as hydraulic sealing system 166, and plug body 128 contacts the compressible material when plug body contacts seat 164.

The technique includes removing plug 122 from the socket 124 (604). In examples, connector 102 causes control circuit 148 to cease providing the electric current to electromagnet 126, 172 in response to a user input received from input device 160, which enables the user to remove plug 122 from socket 124 without having to overcome the pulling force applied by the magnetic field. In examples, control circuit 148 ceases providing the electric current to electromagnet 126, 172 using switch 150. In some examples, plug 122 is configured to unmate from socket 124 when plug 122 is translated in a direction D2 substantially opposite the direction D1. Switch 150 may be configured to de-actuate (e.g., open) when plug 122 unmates from socket 124. In examples, switch 150 is configured to de-actuate control circuit 148 may be configured to de-actuate when skirt 158 displaces from socket 124 as plug 122 unmates from socket 124. Pin 156 may be configured to translate to cause switch 150 to de-actuate when plug 122 unmates from socket 124.

The present disclosure includes the following examples.

Example 1: A connector comprising: a plug defining a channel extending between a plug inlet defined by the plug and a plug outlet defined by the plug, wherein the plug inlet is configured to mechanically engage a first conduit, and wherein the plug defines a plug armature; a socket configured to mechanically engage a second conduit, wherein the plug is configured to mechanically mate with the socket; an electromagnet configured to generate a magnetic field when the electromagnet receives an electric current; and a control circuit configured to provide the electric current to the electromagnet, wherein the plug is configured to cause the control circuit to provide the electric current to the electromagnet when the plug mechanically mates with the socket, and wherein the electromagnet is configured to cause the magnetic field to generate a magnetic force on the plug armature to help sustain the mechanical mating of the plug and the socket.

Example 2: The connector of example 1, wherein the plug is configured to mechanically mate with the socket when the plug translates in a first direction, and wherein electromagnet is configured to cause the electromagnetic field to generate the magnetic force on the armature in a direction substantially perpendicular to the first direction.

Example 3: The connector of example 1 or example 2, wherein the plug includes a plug body defining the channel, and wherein the armature is configured to transmit at least a portion of the magnetic force to the plug body to help sustain the mechanical mating of the plug and the socket.

Example 4: The connector of any of examples 1-3, wherein the socket is configured to fluidly couple the plug inlet and the second conduit when the plug mechanically mates with the socket and the socket mechanically engages the second conduit.

Example 5: The connector of any of examples 1-4, wherein the armature is configured to establish a sliding fit with a wall of the socket when the plug mechanically mates with the socket.

Example 6: The connector of any of examples 1-5, wherein the socket includes a socket body defining a socket well, and wherein the plug is configured to insert into the socket well when the plug mechanically mates with the socket.

Example 7: The connector of any of examples 1-6, wherein the electromagnet is configured to generate the magnetic field within the socket well when the electromagnet receives the electric current.

Example 8: The connector of any of examples 1-7, wherein the socket includes a socket body, and wherein the socket body is configured to form a magnetic circuit with the armature when the when the plug mechanically mates with the socket and the electromagnet generates the magnetic field.

Example 9: The connector of any of examples 1-8, wherein the electromagnet includes one or more pole pieces configured to surround a portion of the plug when the plug mechanically mates with the socket.

Example 10: The connector of any of examples 1-9, wherein the control circuit includes a switch configured to cause the control circuit to provide the electric current to the electromagnet, and wherein the plug is configured to actuate the switch when plug mechanically mates with the socket.

Example 11: The connector of example 10, wherein the socket includes a sliding pin configured to translate and cause closure of the switch, wherein the plug is configured to cause translation of the sliding pin to close the switch when plug mechanically mates with the socket.

Example 12: The connector of any of examples 1-11, further comprising a current source configured to provide the electric current to the electromagnet.

Example 13: The connector of any of examples 1-12, wherein the control circuit is configured to provide a signal to an output device configured to provide an output discernable by a patient when the control circuit provides the electric current to the electromagnet.

Example 14: The connector of any of examples 1-13, wherein the plug includes a plug body, and wherein the armature is configured to surround a periphery of the plug body.

Example 15: A medical system comprising: the connector of any of examples 1-14; tubing defining the first conduit; and a dialysis machine comprising the second conduit.

Example 16: The connector of any of examples 1-15, further comprising an input device configured to receive a user input and provide the user input to the control circuit, wherein the control circuit is configured to cease providing the electric current to the electromagnet in response to the user input.

Example 17: A connector comprising: a plug defining a channel extending between a plug inlet defined by the plug and a plug outlet defined by the plug, wherein the plug inlet is configured to mechanically engage a first conduit, and wherein the plug defines an armature; a socket comprising a socket body defining a socket well, wherein the socket is configured to mechanically engage with a second conduit, and wherein the plug is configured to mechanically mate with the socket when the plug translates in a first direction; an electromagnet configured to generate a magnetic field within the socket well when the electromagnet receives an electric current; and a control circuit configured to provide the electric current to the electromagnet, wherein the plug is configured to cause the control circuit to provide the electric current to the electromagnet when the plug mechanically mates with the socket, wherein the socket body is configured to form a magnetic circuit with the armature when the plug mechanically mates with the socket and the electromagnet generates the magnetic field, and wherein the electromagnet is configured to cause the electromagnetic field to generate a magnetic force on the armature in a direction toward a socket wall of the socket wall to help sustain the mechanical mating of the plug and the socket.

Example 18: The connector of example 17, wherein the armature is configured to establish a sliding fit with the socket wall when the plug mechanically mates with the socket.

Example 19: A method, comprising: mechanically mating a plug and a socket, wherein the plug defines a plug inlet, a plug outlet, and a channel extending between the plug inlet and the plug outlet, wherein the plug inlet is configured to mechanically engage a first conduit, and wherein the socket is configured to mechanically engage a second conduit, wherein when the plug mechanically mates with the socket, a control circuit provides an electric current to energize an electromagnet to help sustain the mechanical mating of the plug with a magnetic force generated on an armature of the plug by a magnetic field produced by the energized electromagnet; and, subsequently, removing the plug from the socket.

Example 20: The method of example 19, further comprising: translating the plug in a first direction to mechanically mate the plug and the socket; and sustaining the mechanical mating with the electromagnetic force generated on the armature in the first direction.

Various examples of the disclosure have been described. Any combination of the described systems, operations, or functions is contemplated. These and other examples are within the scope of the following claims.

What is claimed is:

1. A connector comprising:
    a socket configured to mechanically mate with a plug, the socket comprising at least one electromagnet configured to generate a magnetic field when the electromagnet receives an electric current, wherein the socket defines a socket well fluidically coupled to a flow channel of a conduit, wherein the socket well is configured to receive the plug when the socket mechanically mates with the plug, and wherein the socket well is configured to fluidically couple a plug channel extending through a body of the plug and the flow channel when the socket mechanically mates with the plug; and
    a control circuit configured to provide the electric current to the electromagnet, the control circuit configured to provide the electric current to the electromagnet when the socket mechanically mates with the plug, and
    wherein the electromagnet is configured to cause the magnetic field to generate a magnetic force on a plug armature of the plug to help sustain the mechanical mating of the plug and the socket when the control circuit provides the electric current.

2. The connector of claim 1, wherein the socket is configured to fluidly couple a plug inlet of the plug channel and the flow channel when the plug mechanically mates with the socket.

3. The connector of claim 1, wherein a wall of the socket is configured to establish a sliding fit with the plug armature when the plug mechanically mates with the socket.

4. The connector of claim 1, wherein the electromagnet is configured to generate the magnetic field within the socket well when the electromagnet receives the electric current.

5. The connector of claim 1, wherein the socket includes a socket wall defining the socket well, and wherein the electromagnet includes one or more pole pieces configured around a portion of the socket wall, wherein the one or more pole pieces are configured to distribute the magnetic field.

6. The connector of claim 1, wherein the control circuit includes a switch configured to cause the control circuit to provide the electric current to the electromagnet, and wherein the switch is configured to be actuated by the plug when the plug mechanically mates with the socket.

7. The connector of claim 6, the socket further comprising a sliding pin configured to translate and cause closure of the switch, wherein the plug is configured to cause translation of the sliding pin to close the switch when plug mechanically mates with the socket.

8. The connector of claim 6, wherein the switch is configured to de-actuate when the plug is mechanically uncoupled from the socket.

9. The connector of claim 6, wherein the switch is a proximity switch configured to de-actuate when the plug is displaced from the socket.

10. The connector of claim 1, further comprising at least one sensor configured to detect a proximity of the socket to the plug.

11. The connector of claim 10, wherein the sensor is one or more of: a potentiometer position sensor, a linear variable differential transformer/voltage displacement (LVDT) transducer, a hall-effect magnetic sensor, a mechanical counter, a cam, or an actuating arm.

12. A system, comprising
    the connector of claim 1; and
    the plug comprising a plug inlet and a plug outlet, wherein the plug channel extends from the plug inlet to the plug outlet, and wherein the plug inlet is configured to mechanically engage a first conduit,
    wherein the socket is configured to mechanically engage a second conduit defining the flow channel, and
    wherein the second conduit is connectable to a medical machine.

13. The system of claim 12, wherein the first conduit is connectable to a container.

14. The system of claim 13, wherein the container is a concentrate container.

15. The system of claim 12, wherein the medical machine is a dialysis machine.

16. The system of claim 12, further comprising an input device configured to receive a user input and provide the user input to the control circuit, wherein the control circuit is configured to cease providing the electric current to the electromagnet in response to the user input.

17. The system of claim 12, further comprising an output device.

18. The system of claim 17, the output device configured to provide an output to a user when the plug mechanically mates with the socket.

19. A system comprising:
    a plug defining a plug inlet, a plug outlet, and a plug channel extending from the plug inlet to the plug outlet;
    a connector comprising a socket configured to mechanically mate with the plug, the socket comprising at least one electromagnet configured to generate a magnetic field when the electromagnet receives an electric current, wherein the socket includes a socket wall defining a socket well fluidically coupled to a flow channel of a conduit, wherein the socket well is configured to receive the plug when the socket mechanically mates with the plug, and wherein the socket is configured to fluidically couple the plug channel and the flow channel when the socket mechanically mates with the plug; and
    a control circuit configured to provide the electric current to the electromagnet, the control circuit configured to provide the electric current to the electromagnet when the socket mechanically mates with the plug,
    wherein the electromagnet is configured to cause the magnetic field to generate a magnetic force on a plug armature of the plug to help sustain the mechanical mating of the plug and the socket when the control circuit provides the electric current, and
    wherein the electromagnet includes one or more pole pieces configured around a portion of the socket wall, the one or more pole pieces configured to distribute the electromagnetic field.

20. The system of claim 19, further comprising an input device configured to receive a user input and provide the user input to the control circuit, wherein the control circuit is configured to cease providing the electric current to the electromagnet in response to the user input.

\* \* \* \* \*